(12) United States Patent
Ding et al.

(10) Patent No.: US 8,980,314 B2
(45) Date of Patent: Mar. 17, 2015

(54) ENTERIC FORMULATION OF DULOXETINE AND ITS CORE AND PREPARATION METHOD

(75) Inventors: Yunhui Ding, Shanghai (CN); Siji Zheng, Shanghai (CN)

(73) Assignee: Shanghai Zhongxi Pharmaceutical Corporation, Shanghai (CN)

( * ) Notice: Subject to any disclaimer, the term of this patent is extended or adjusted under 35 U.S.C. 154(b) by 568 days.

(21) Appl. No.: 13/142,116

(22) PCT Filed: Nov. 4, 2009

(86) PCT No.: PCT/CN2009/074786
§ 371 (c)(1),
(2), (4) Date: Jul. 27, 2011

(87) PCT Pub. No.: WO2010/072105
PCT Pub. Date: Jul. 1, 2010

(65) Prior Publication Data
US 2011/0274750 A1    Nov. 10, 2011

(30) Foreign Application Priority Data

Dec. 26, 2008 (CN) .......................... 2008 1 0207877

(51) Int. Cl.
A61K 9/48 (2006.01)
A61K 31/381 (2006.01)
A61K 9/28 (2006.01)
A61K 9/50 (2006.01)

(52) U.S. Cl.
CPC ............ *A61K 31/381* (2013.01); *A61K 9/2886* (2013.01); *A61K 9/5073* (2013.01); *A61K 9/5089* (2013.01)
USPC ....................................................... 424/463

(58) Field of Classification Search
None
See application file for complete search history.

(56) References Cited

U.S. PATENT DOCUMENTS

| 5,508,276 A | 4/1996 | Anderson et al. |
| 2007/0184113 A1 | 8/2007 | Chatterji et al. |
| 2011/0150942 A1* | 6/2011 | Zajc et al. ................... 424/400 |

FOREIGN PATENT DOCUMENTS

| CN | 1759829 A | 4/2006 |
| CN | 1759830 A | 4/2006 |
| CN | 101190208 A | 6/2008 |
| WO | 2007-034503 A2 | 3/2007 |
| WO | 2007-082809 A1 | 7/2007 |
| WO | 2008129501 A2 | 10/2008 |

OTHER PUBLICATIONS

CN 101190208A—machine translation, Jun. 4, 2008.*
Mannitol entry from Wikipedia [online] [downloaded Apr. 25, 2013 from en.wikipedia.org/wiki/Mannitol.*
Crowley et al., Drug Dev Industrial Pharmacy 33: 909-926 (2007).*
Ghebremeskel et al., Int J Pharmaceutics 328: 119-129 (2007).*
PEG 6000 MSDS [downloaded Nov. 11, 2013 from http://web.archive.org/web/20061102040621/http://www.metlabcorp.com/msds/CUTTINGFLUIDS.pdf].*
International Search Report for PCT/CN2009/074786 mailed Feb. 11, 2010.
Written Opinion corresponding to PCT/CN2009/074786, mailed Feb. 11, 2010.
Extended European Search Report corresponding to EP 09834058.1, dated Jun. 27, 2012.
Office Action corresponding to 200810207877.2, dated Dec. 28, 2010.
Office Action issued in European Patent Application No. 09834058.1 dated Jul. 24, 2013. (4 pages).

* cited by examiner

*Primary Examiner* — Sue Liu
*Assistant Examiner* — Thor Nielsen
(74) *Attorney, Agent, or Firm* — Lowe Hauptman & Ham, LLP

(57) ABSTRACT

An enteric formulation of duloxetine, its core and preparing method thereof are disclosed. The core comprises duloxetine or its salt and pharmaceutically acceptable excipients. The excipients include water-soluble hot melt materials selected from PEG, poloxamer, polyoxyl (40) stearate or their mixture. Based on the total weight of the core, the amount of water-soluble hot melt materials is 10%~40% and the amount of duloxetine or its salt is 15~60%. The core material is prepared by hot melt process. The enteric formulation comprises the core, a separating layer and an enteric layer.

16 Claims, 1 Drawing Sheet

ENTERIC FORMULATION OF DULOXETINE AND ITS CORE AND PREPARATION METHOD

RELATED APPLICATIONS

The present application is a National Phase of International Application Number PCT/CN2009/074786, filed Nov. 4, 2008 and claims priority from, Chinese Application Number 200810207877.2, filed Dec. 26, 2008.

TECHNICAL FIELD

The present invention belongs to the field of pharmaceutical formulation, especially relates to an enteric formulation of duloxetine, its core and preparing method thereof.

BACKGROUND OF THE INVENTION

Duloxetine is a selective serotonin and norepinephrine reuptake inhibitors (SNRIs). It is a safe and effective antidepressant drug. Its chemical designation is (+)-(S)—N-methyl-γ-(1-naphthyloxy)2-thiophenepropylamine. It is usually used in the form of its hydrochloride. As duloxetine is unstable and easily degraded in acidic condition, it is suitable to make duloxetine or its salts into enteric formulation to resist the corrosion of gastric juice.

U.S. Pat. No. 5,508,276 relates to a kind of duloxetine enteric pellet, which comprising a) a core consisting of duloxetine and a pharmaceutically acceptable excipient; b) an optional separating layer; c) an enteric layer comprising hydroxypropyl methylcellulose acetate succinate (HPMCAS) and a pharmaceutically acceptable excipient; d) an optional finishing layer. In the separating layer, sugar alleviates the migration and interaction between enteric coating material and duloxetine to improve the acid resistance and stability.

Z1200410067160.4 relates to a kind of duloxetine enteric coating tablet and manufacturing process thereof. Duloxetine hydrochloride, water-soluble solid disperse carrier and thinner are dissolved in ethanol aqueous; it is to be sieved and pelletized, dried, granulated, added lubricant and then preformed using the methods commonly known in this field; and the tablet core is coated with separating layer and the separating layer is coated with enteric layer. This method uses solid dispersion technology, increases the solubility of the main drug and improves the final release amount so as to improve the bioavailability of duloxetine.

Duloxetine easily tends to take place reactions of degradation etc. In which water plays an accelerated or catalytic role. As for the published duloxetine hydrochloride enteric formulation, during the manufacture of the medicine core of duloxetine hydrochloride, the solution or suspension of duloxetine hydrochloride is made first, or the wetting agent or adhesion agent is added first, and in both conditions, duloxetine hydrochloride has contacted with water and some organic solvents such as ethanol, which influences the stability of duloxetine hydrochloride; moreover, when removing the water or the organic solvents, it wastes time and labor force and increases cost, and the unstable factor will also be increased. If the organic solvents are used, it will be an environmental pollution.

SUMMARY OF THE INVENTION

The technical problem to be solved by the present invention is to overcome the disadvantage that the unstable factor of the pharmaceutical active ingredient duloxetine is increased and the solvents are remained as water or organic solvent is contacted during the preparation of the medicine core of duloxetine, and to provide a new medicine core of duloxetine and enteric formulation thereof and manufacturing process thereof. During the preparation of the said medicine core of duloxetine, neither water nor organic solvent is contacted, the degradation of the pharmaceutical active ingredient duloxetine is less, the duloxetine is stable, the content of the pharmaceutical active ingredient is high, and the dissolution is good.

The inventor has tried preparing the medicine core of duloxetine hydrochloride without addition of solvents such as water. But as the specific gravity of duloxetine hydrochloride is small, and the flowability is not good, duloxetine hydrochloride cannot be mixed thoroughly with other excipient. So it is difficult to conduct the method of direct pression of the medicine core in the form of powder. Duloxetine hydrochloride is loose, its viscosity is bad, and it is difficult to be mixed in dry form, so it forms poorly and the yield is low when the pelletization method of squeeze is used. The hot melt method can mix the medicine and the excipient without water or organic solvent. And the hot melt method doesn't only mix the medicine and the excipient well, but also finishes the forming of the medicine core at the same time. Therefore, the inventor prepares the medicine core and enteric formulation of duloxetine using the hot melt method. After effect experiments, the obtained duloxetine enteric formulation satisfies the purpose of this invention completely and this invention is completed.

Consequently, one of the technical solutions used to resolve the technical problem mentioned above is that a medicine core of duloxetine enteric formulation consisting of pharmaceutical active ingredient duloxetine or its salt and pharmaceutically acceptable excipient. Wherein, the pharmaceutically acceptable excipient contains water-soluble hot melt materials, the content of which is 10%~40%. The content of pharmaceutical active ingredient duloxetine or its salt is 15%~60%. And the rest is other pharmaceutically acceptable excipient. The percentage mentioned above is which they account for the total mass of the medicine core.

According to this invention, the said water-soluble hot melt materials are the pharmaceutically acceptable water-soluble materials which are solid in the environment of 18~26° C., and can be soften or melt by heating. The preferable softening or melting temperature of the said water-soluble hot melt material is 40~65° C. On one hand, the water-soluble hot melt materials in this invention have specific softening or melting temperature so that it produces adhesive force after it melts, and it is solid again when it is in room temperature, which satisfies the need of melt-granulation. On the other hand, its water-solubility can make the main drug release from the tablet core. The said water-soluble hot melt material is preferably one or more selected from the group consisting of polyethyleneglycol (PEG), poloxamer and polyoxyl (40) strarate. The said polyethyleneglycol is preferably one or more selected from polyethyleneglycol 4000~10000. It is preferred, the content of the said water-soluble hot melt material is 5%~40%, more preferably is 10~25%; the percentage of the water-soluble hot melt material accounts for the total mass of the medicine core.

According to this invention, the said duloxetine salt is preferably duloxetine hydrochloride. The content of duloxetine or its salt is preferably 15%~60%; the percentage of duloxetine or its salt accounts for the total mass of the medicine core. The average diameter of the said duloxetine or its salt is preferably less than 100 μm.

According to this invention, the said other pharmaceutically acceptable excipient is preferably one or more selected from the group consisting of filler, disintegrant, lubricant and surfactant. The said filler is preferably one or more selected from the group consisting of sucrose, mannitol, xylitol, glucose, maltol, sorbitol, hydroxypropyl-β-cyclodextrin, starch, microcrystalline cellulose, pre-colloidization starch, magnesium oxide, arginine, magnesium carbonate, sodium carbonate, sodium bicarbonate and calcium hydrogenphosphate dihydrate, and more preferably one or more selected from the group consisting of sucrose, mannitol, xylitol, maltol, hydroxypropyl-β-cyclodextrin, microcrystalline cellulose, pre-colloidization starch, magnesium oxide, arginine, sodium carbonate, sodium bicarbonate and magnesium carbonate. The studies in this invention show that some sugar and sugar alcohol are not only beneficial to the release of the main drug from the medicine core, but also beneficial to the stability of the main drug, especially sucrose, mannitol, xylitol and maltol. Otherwise, using lactose as the main filler will affect the stability of the preparation, thus lactose is not the preferable filler. The content of the said filler may be 0%~65% of the mass of the medicine core, preferably 0%~65%, and more preferably 20%~50%.

According to this invention, the said disintegrant is preferably selected from the group consisting of sodium starch glycolate, hydroxypropyl cellulose, crospovidone and croscarmellose sodium, and more preferably selected from the group consisting of sodium starch glycolate crospovidone and croscarmellose sodium. The content of the said disintegrant may be 0%~18% of the mess of the medicine core, preferably 1%~18%, and more preferably 2%~10%.

According to this invention, the said lubricant may be selected from the conventional materials of pharmaceutical formulation, and preferably one or more selected from the group consisting of magnesium stearate, colloidal silicon dioxide, sodium stearyl fumarate and talc. The content of the said lubricant may be 0%~3% of the mass of the medicine core, preferably 0.1%~3%, and more preferably 0.5%~1.5%. The said surfactant may be selected from the conventional materials of pharmaceutical formulation, and preferably selected from the group consisting of Tween-80, polyoxyethylene castor oil and sodium lauryl sulfate etc. The content of the said surfactant may be 0%~3% of the mass of the medicine core, preferably 0.1%~1.5%.

The second technical solution used to resolve the technical problem mentioned above is a manufacturing process of the medicine core of the duloxetine enteric formulation mentioned above, which contains the following steps: mixing duloxetine or its salt, water-soluble hot melt material and pharmaceutically acceptable excipient, heating the water-soluble hot melt materials until they are softened or melted, and granulating in the state that the water-soluble hot melt materials are softened or melted, then just cooling down.

According to this invention, the said granulation is preferably hot melting stirring granulation, hot melting fluidifying granulation or hot melting squeezing granulation. Wherein, in the said hot melting stirring granulation, the materials are put into the jacket heating granulation container. The triaxial mixing blade is turned on and turns at a certain speed. The materials are heated to the temperature needed by the jacket of the granulation container. The hot melt materials produce adhesive action when they are melted, which make the materials become soft materials. The soft materials turn over and rotate along the wall in the container. The massive materials are broken into pieces by slickers rotating in high speed. By the rubbing of the particles with the task wall and the gathering and rubbing of the particles, the granules are formed. The said hot melting fluidifying granulation is done in the fluidized bed granulator. In which the materials are heated to the temperature needed by hot air. In the fluidifying process of the materials, the hot melt materials produce adhesive action when they are melted which make the powder gather around them to form the particle cores. As the combination between one particle core and another, and the combination between particle core and particle go on, larger granules are formed. In the said hot melting squeezing granulation, the materials are mixed and put into the jacket heating and warming squeezing container. After the hot melt materials are melted, the materials become wet materials. The wet materials are squeezed through the sieve plate with certain aperture by propeller propulsion to get the cylindrical banding extrudate which is cut off at once to form the granules.

According to this invention, in the said hot melting stirring granulation, the amount of the hot melting materials, the stirring time of granulation, the temperature in the jacket and the temperature of the materials have great influence on the property, the forming and the quality of the granules. The stirring time of granulation can be controlled based on adjusting of the constituent and amounts of the hot melting materials. The preferable stirring time is controlled within 10 minutes when the hot melting materials reach the melt temperature. The temperature in the jacket is commonly 60~90° C., and it can be controlled in 15~25° C. higher than the melt temperature of the hot melting materials based on the different constituent of the melting materials. All of these are beneficial to the preparation of granules with good compressibility and good fluxility.

The third technical solution used to resolve the technical problem mentioned above is a duloxetine enteric formulation which contains a medicine core, a separating layer and an enteric layer. Wherein, the said medicine core is the medicine core mentioned above.

According to this invention, the said duloxetine enteric formulation is preferably enteric-coated tablet, enteric granules or enteric micro-tablet capsule. Wherein, as for the said enteric coated tablet or enteric granules, the medicine core in this invention mentioned above is coated in sequence with a separating layer and an enteric layer. The said enteric micro-tablet capsule is a common hard capsule within the medicine core mentioned above coated with the separating layer and the enteric layer.

As the common enteric formulation in this field, the said separating layer can comprise kinds of the separating layer materials that are common in this field. Preferably, it can be one or more selected from the group consisting of hypromellose, hydroxypropyl cellulose and methylcellulose. The separating layer can also contain sugar and xylitol further which can increase the stability of the enteric formulation of duloxetine or its salts; and it can also contain other pharmaceutical excipients selected from the group consisting of filling excipient, opacifier, plasticizer and anti-adhesive agent etc. As the common enteric formulation in this field, the said enteric layer can contain the enteric materials commonly used in the field of pharmaceutical formulation. Preferably, the enteric materials can be one or more selected from the group consisting of acrylic, polyvinyl alcohol phthalate, hydroxypropylmethylcellulose acetate succinate (HPMCAS) and hydroxypropylmethyl cellulose phthalate (HPMCP). The said enteric layer can preferably also contain plasticizer further. The said plasticizer is preferably one or more selected from the group consisting of triethyl citrate, diethyl phthalate, methyl silicone oil, castor oil and polyethylene glycol. The enteric layer can also contain other pharmaceutical excipients further such as anti-adhesive agent, lubricant, surfactant etc.

There can also be modified layer outside the said enteric layer, but not necessarily. In some prescriptions, the moistureproof ability of the enteric formulation during storage can be increased and the appearance will be more intact and more glabrous by selecting proper modified layer. Preferably, the said modified layer can contain one or more selected from the group consisting of film-former of hypromellose etc., talc, silicon dioxide, titanium dioxide, polyethylene glycol or hydrophobic materials such as wax etc.

The fourth technical solution used to resolve the technical problem mentioned above is a manufacturing process of the duloxetine enteric formulation mentioned above which contains the following steps:
(1) Coating the medicine core mentioned above with the separating layer using the common manufacturing procedure in this field;
(2) Coating with the enteric layer using the common manufacturing procedure in this field.

According to this invention, the said manufacturing process of the duloxetine enteric formulation can also contain the step: (3) Coating with the modified layer.

All the raw materials and reagents in this invention are commercially available unless specified.

In comparison with the existing technologies, the beneficial effects of this invention is as follows: in this invention, the medicine core of the enteric formulation of duloxetine or its salt is prepared using hot-melt technique, which avoids the introduction of water or organic solvents, reduces the residual of solvents, also decreases the degradation of duloxetine, and increases the stability of the formulation in preparation and storage. The adhesive is not needed to add and the granules are not needed to dry in this invention, which simplifies the manufacture steps greatly and reduces wear and tear. The cost is reduced as well. The hot melting materials in this invention such as polyethylene glycol, poloxamer and polyoxyl (40) stearates are hydrosoluble, which achieves the release of the main drug from the medicine core and make dissolution rate be good and increases the biological availability of the medicine. The content of the active pharmaceutical ingredients of the enteric formulation of duloxetine or its salt in this invention is high.

BRIEF INTRODUCTION OF THE DRAWINGS

The feature and beneficial effects of this invention are illuminated in combination with the drawings.

SPECIFIC MODE FOR CARRYING OUT THE INVENTION OR UTILITY MODEL

Figure 1:
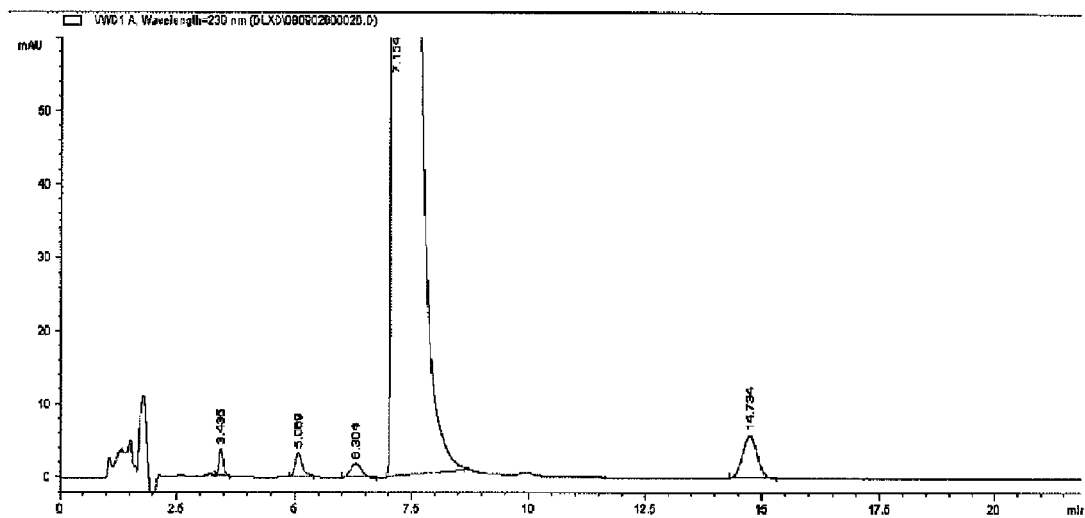
FIG. 1 is the determination spectrogram of related substances of the medicine core of duloxetine hydrochloride prepared by common wet granulation method, which is sealed up in high density polyethylene bottle and placed in the temperature of 40° C.±2° C. and the relative humidity of 75%±5%.

The following examples are used to further explain this invention, but not to restrict the scope of this invention. In the following examples the experimental methods which are not indicated by the actual conditions are usually done in the common conditions or conditions suggested by the manufacturer. Wherein, the softening temperature of polyethylene glycol 4000~10000 is 48~63° C., the melt temperature of poloxamer is 49~57° C., and the melt temperature of polyoxyl (40) stearates is 46~51° C.

Example 1

Enteric Tablet (Convert to 1.2 kg)

Bill of Materials:

| the medicine core | |
| --- | --- |
| duloxetine hydrochloride | 187.2 g |
| sucrose | 500.4 g |
| PEG6000 | 169.2 g |
| microcrystalline cellulose | 250.2 g |
| crospovidone | 86.4 g |
| magnesium stearate | 6.2 g |
| the separating layer | |
| hypromellose | 31.8 g |
| talc | 15.6 g |
| sucrose | 40.0 g |
| titanium dioxide | 6.3 g |
| the enteric layer | |
| Acryl-EZE ® MP | 74.9 g |
| methyl silicone oil | 0.37 g |

Manufacturing Process:

The duloxetine hydrochloride, sucrose, microcrystalline cellulose, 70% amount of polyvinylpolypyrrolidone and PEG6000 were mixed homogeneously, and placed into the high speed agitator with the temperature in the jacket of 80~85° C. The agitator of the granulator was turned on. When the temperature of the materials reached 60° C., the agitation went on for 6 min. The materials were gave out, cooled down, and granulated by 24 mesh sieve. The remaining crospovidone and magnesium stearate were added, mixed homogeneously, and squashed. Then the medicine core was obtained.

The duloxetine hydrochloride enteric tablet was prepared in this example. The manufacturing process of coating is that: after the hypromellose was dispersed using hot water of 70° C., then water was added and stirred to dissolve. The homogenized talc and titanium dioxide were added. The solution of separating layer with the solid content of about 15 wt % was prepared. The medicine core was placed into the coating pan. Adjusting the entering air temperature to make the temperature of the tablet bed be 30~40° C. and the nebulized pressure be 4.0 kg/cm². The rotation rate of the cauldron was 12 rpm. The separating layer was coated the medine core.

The Acryl-EZE®MP was prepared to an aqueous dispersion with a solid content of about 20 wt %. Then the methyl silicone oil of 0.5 wt % of the amount of the Acryl-EZE® MP was added and stirred for 20 min. Adjusting the entering air temperature to make the temperature of the tablet bed be 28~32° C. and the nebulized pressure be 2.0 kg/cm². The rotation rate of the cauldron was 12 rpm. The enteric layer was coated the medine core.

Example 2

Enteric Coated Tablet

Bill of Materials:

| the medicine core | |
|---|---|
| duloxetine hydrochloride | 33.6 mg |
| sucrose | 115.9 mg |
| PEG6000 | 25.7 mg |
| crospovidone | 13.6 mg |
| magnesium stearate | 1.8 mg |
| the separating layer | |
| hypromellose | 8.1 mg |
| talc | 8 mg |
| sucrose | 4.1 mg |
| titanium dioxide | 1.6 mg |
| the enteric layer | |
| acrylic resin aqueous dispersion (L30D-55) | 35.8 mg |
| triethyl citrate | 1.2 mg |
| talc | 1.2 mg |

Manufacturing Process:

The duloxetine hydrochloride, sucrose, 70% amount of crospovidone and PEG6000 were mixed homogeneously, and placed into the high speed agitator with the temperature in the jacket of 80~85° C. The agitator of the granulator was turned on. When the temperature of the materials reached 60° C., the agitation went on for 8 min. The materials were gave out, cooled down, and granulated using 24 mesh sieve. The remaining crospovidone and magnesium stearate were added, mixed homogeneously, and squashed. Then the medicine core was obtained.

The duloxetine hydrochloride enteric tablet was prepared in this example. The manufacturing process of coating is that: after the hypromellose was dispersed using hot water of 70° C., then water was added and stirred to dissolve. The homogenized talc and titanium dioxide were added. The solution of separating layer with the solid content of about 15 wt % was prepared. The medicine core was placed into the coating pan. Adjusting the entering air temperature to make the temperature of the tablet bed be 30~40° C. and the nebulized pressure be 2.0 kg/cm². The rotation rate of the cauldron was 20 rpm. The separating layer was coated the medine core.

The operation of the enteric layer: the triethyl citrate and talc were added to water and homogenized sufficiently for 5~10 min with high shear pulp refiner, then was added to the aqueous dispersion of acrylic resin, stirred slowly for 30 min, and passed through 80 mesh fineness to make the solution of the enteric layer with the solid content of about 20 wt %. The medicine core coated with the separating layer was placed into the coating pan to be coated with the enteric layer.

Example 3

Enteric Tablet

Bill of Materials:

| the medicine core | |
|---|---|
| duloxetine hydrochloride | 33.6 mg |
| maltitol | 99.6 mg |
| PEG6000 | 34.3 mg |
| Hydroxypropyl cellulose | 17.7 mg |
| arginine | 10 mg |
| crospovidone | 3.6 mg |
| colloidal silicon dioxide | 0.3 mg |
| magnesium stearate | 1 mg |
| the separating layer | |
| hypromellose | 5.1 mg |
| talc | 10 mg |
| titanium dioxide | 1 mg |
| the enteric layer | |
| HPMCAS-LF | 13.7 mg |
| triethyl citrate | 3.83 mg |
| talc | 4.1 mg |
| sodium lauryl sulfate | 0.4 mg |

Manufacturing Process:

The duloxetine hydrochloride, maltitol, hydroxypropyl cellulose, arginine and PEG6000 were mixed homogeneously, and made into granules as Example 2. The colloidal silicon dioxide and magnesium stearate were added, mixed homogeneously and squashed. Then the medicine core was obtained.

The operation of the separating layer was the same as Example 2 above.

The operation of the enteric layer:

First, the triethyl citrate was dissolved in water. The solution was cooled down to 10° C. HPMCAS-LF, sodium lauryl sulfate and talc were added slowly and carefully to make a 75% (W/V) suspension of HPMCAS-LF. The medicine core was placed into the coating pan and coated with the enteric layer.

Example 4

Enteric Tablet

Bill of Materials:

| the medicine core | |
|---|---|
| duloxetine hydrochloride | 33.6 mg |
| sucrose | 99.6 mg |
| PEG6000 | 34.3 mg |
| pregelatinized starch | 15.7 mg |
| sodium bicarbonate | 12 mg |
| crospovidone | 3.6 mg |
| colloidal silicon dioxide | 1 mg |
| magnesium stearate | 1 mg |
| the separating layer | |
| hypromellose | 5.1 mg |
| talc | 10 mg |
| titanium dioxide | 1 mg |
| the enteric layer | |
| HPMCP-55S | 14.3 mg |
| talc | 4.29 mg |
| dichloromethane | 107 mg |
| ethanol | 133.6 mg |
| water | 26.9 mg |

Manufacturing Process:

The duloxetine hydrochloride, sucrose, pregelatinized starch, sodium bicarbonate and PEG6000 were mixed homogeneously, and made into granules in the same manner as Example 2 above. The colloidal silicon dioxide, magnesium stearate and crospovidone were added, mixed homogeneously and squashed. Then the medicine core was obtained.

The operation of the separating layer was the same as Example 2 above.

The operation of the enteric layer:

HPMCP-55S was added to the mixed solution of ethanol and dichloromethane with stirring to mix homogeneously. The talc was added to water, stirred homogeneously, and added to the above mixed solution of ethanol and dichloromethane slowly. Keeping stirring until they dissolve thoroughly. The 5 wt % suspension of HPMCP-55S was passed through the 24 mesh sieve. The medicine core was coated with the enteric layer.

Example 5

Enteric Tablet

Bill of Materials:

| the medicine core | |
|---|---|
| duloxetine hydrochloride | 33.6 mg |
| sucrose | 100.6 mg |
| PEG6000 | 33.4 mg |
| microcrystalline cellulose | 28.0 mg |
| crospovidone | 2.1 mg |
| magnesium stearate | 1 mg |
| the separating layer | |
| hypromellose | 8 mg |
| talc | 5 mg |
| sucrose | 3 mg |
| the enteric layer | |
| acrylic resin aqueous dispersion (L30D-55) | 35.8 mg |
| triethyl citrate | 1.2 mg |
| talc | 1.2 mg |

Manufacturing Process:

The operation of granulation, the separating layer and the enteric layer were the same as Example 2 above.

Example 6

Enteric Tablet

Bill of Materials:

| the medicine core | |
|---|---|
| duloxetine hydrochloride | 33.6 mg |
| mannitol | 77.7 mg |
| pregelatinized starch | 24.3 mg |
| PEG4000 | 29.0 mg |
| PEG8000 | 31.1 mg |
| crospovidone | 2.0 mg |
| magnesium stearate | 1.5 mg |
| the separating layer | |
| Opadry 03K19229 | 8 mg |
| the enteric layer | |
| Acryl-Eze ® MP | 12 mg |
| Methyl silicone oil | 0.06 mg |

Manufacturing Process:

The duloxetine hydrochloride, mannitol, pregelatinized starch, PEG4000, PEG8000 and 70% amount of the crospovidone were mixed homogeneously, and made into granules in the same manner as Example 2 above. The remaining crospovidone and magnesium stearate were added, mixed homogeneously and squashed. Then the medicine core was obtained.

The operation of the separating layer: Opadry 03K19229 (OPADRY CLEAR 03K19229) was homodispersed in water of about 80° C., high speed sheared for 10 minutes, and stirred for another 45 minutes to make a solution with the solid content of about 15 wt %. The medicine core was coated with the separating layer.

The operation of the enteric layer was the same as Example 1 above.

Example 7

Enteric Tablet

Bill of Materials:

| the medicine core | |
|---|---|
| duloxetine hydrochloride | 33.6 mg |
| mannitol | 78.1 mg |
| sodium starch glycolate | 24.3 mg |
| poloxamer | 17.3 mg |
| PEG8000 | 16.3 mg |
| crospovidone | 1.9 mg |
| colloidal silicon dioxide | 0.3 mg |
| magnesium stearate | 0.8 mg |
| the separating layer | |
| hypromellose | 7 mg |
| talc | 20 mg |
| the enteric layer | |
| acrylic resin aqueous dispersion (L30D-55) | 35.8 mg |
| triethyl citrate | 1.2 mg |
| talc | 1.2 mg |
| the modified layer | |
| hypromellose | 4.6 mg |
| talc | 1.5 mg |
| titanium dioxide | 1.6 mg |

Manufacturing Process:

The duloxetine hydrochloride, mannitol, sodium starch glycolate, poloxamer and PEG8000 were mixed homogeneously, and made into granules in the same manner as Example 2 above. crospovidone, colloidal silicon dioxide and magnesium stearate were added, mixed homogeneously and squashed. Then the medicine core was obtained.

The operation of the separating layer and the enteric layer were the same as Example 2 above. The operation of the modified layer: hypromellose was dispersed in hot water of 70° C., and then water was added and stirred to dissolve. Homogenized talc and titanium dioxide were added to make a solution of the modified layer with the solid content of about 15 wt %. The medicine core was placed into the coating pan and coated with the modified layer.

Example 8

Enteric Tablet

Bill of Materials:

| the medicine core | |
|---|---|
| duloxetine hydrochloride | 33.6 mg |
| maltitol | 73.1 mg |

-continued

| | |
|---|---|
| hydroxypropyl-β-cyclodextrin | 18.5 mg |
| polyoxyl (40) stearate | 17.7 mg |
| PEG8000 | 16.7 mg |
| crospovidone | 1.9 mg |
| magnesium carbonate | 6 mg |
| magnesium stearate | 0.8 mg |
| the separating layer | |
| hypromellose | 6.2 mg |
| talc | 6.0 mg |
| titanium dioxide | 1.6 mg |
| the enteric layer | |
| acrylic resin aqueous dispersion (L30D-55) | 35.8 mg |
| triethyl citrate | 1.2 mg |
| talc | 1.2 mg |
| The modified layer | |
| hypromellose | 4.6 mg |
| talc | 1.5 mg |

Manufacturing Process:

The duloxetine hydrochloride, maltitol, hydroxypropyl-β-cyclodextrin, polyoxyl (40) stearate, magnesium carbonate and PEG8000 were mixed homogeneously, and made into granules in the same manner as Example 2 above. crospovidone and magnesium stearate were added, mixed homogeneously and squashed. Then the medicine core was obtained.

The operation of the separating layer and the enteric layer were the same as Example 2 above. The operation of the modified layer referred to Example 7.

Example 9

Enteric Tablet (Fluidized Granulation)

Bill of Materials:

| the medicine core | |
|---|---|
| duloxetine hydrochloride | 33.6 mg |
| sucrose | 82.0 mg |
| PEG6000 | 34 mg |
| microcrystalline cellulose | 25.4 mg |
| sodium carbonate | 5 mg |
| crospovidone | 14.2 mg |
| magnesium stearate | 1 mg |
| the separating layer | |
| hypromellose | 5.1 mg |
| talc | 10 mg |
| titanium dioxide | 1 mg |
| the enteric layer | |
| Acryl-Eze ® MP | 12 mg |

Manufacturing Process:

The operation of granulation: the duloxetine hydrochloride, sucrose, microcrystalline cellulose, sodium carbonate, PEG6000 and 70% amount of crospovidone were mixed homogeneously. The fluidized bed granulator was turned on, and the air ratio of the fan was set to 12~15 Hz, until the temperature of the materials was 60~65° C. The materials were gave out, cooled down, and granulated using 24 mesh sieve. The remaining crospovidone and magnesium stearate were added, mixed homogeneously and squashed. Then the medicine core was obtained.

The operation of the separating layer and the enteric layer were the same as Example 1 above.

Example 10

Enteric Tablet

Bill of Materials:

| the medicine core | |
|---|---|
| duloxetine hydrochloride | 33.6 mg |
| sucrose | 40.5 mg |
| PEG6000 | 19.8 mg |
| microcrystalline cellulose | 10.5 mg |
| crospovidone | 12.1 mg |
| colloidal silicon dioxide | 0.3 mg |
| magnesium stearate | 1 mg |
| the separating layer | |
| OPADRY CLEAR 03K19229 | 4.3 mg |
| the enteric layer | |
| Acryl-Eze ® MP | 6.5 mg |
| Methyl silicone oil | 0.032 mg |

Manufacturing Process:

The duloxetine hydrochloride, sucrose, microcrystalline cellulose, 70% amount of crospovidone and PEG6000 were mixed homogeneously, and made into granules in the same manner as Example 2 above. The remaining crospovidone, colloidal silicon dioxide and magnesium stearate were added, mixed homogeneously and squashed. Then the medicine core was obtained.

The operation of the separating layer was the same as Example 6 above; the operation of the enteric layer was the same as Example 2 above.

Example 11

Enteric Tablet

Bill of Materials:

| the medicine core | |
|---|---|
| duloxetine hydrochloride | 33.6 mg |
| sucrose | 35.2 mg |
| PEG6000 | 8.0 mg |
| crospovidone | 6.1 mg |
| colloidal silicon dioxide | 0.2 mg |
| magnesium stearate | 0.8 mg |
| the separating layer | |
| hypromellose | 3.6 mg |
| talc | 3.2 mg |
| titanium dioxide | 0.72 mg |
| the enteric layer | |
| acrylic resin aqueous dispersion (L30D-55) | 21.3 mg |
| triethyl citrate | 0.7 mg |
| talc | 0.7 mg |

Manufacturing Process:

The operation of granulation, the separating layer and the enteric layer were the same as Example 2 above.

Example 12

Enteric Tablet

Bill of Materials:

| the medicine core | |
|---|---|
| duloxetine hydrochloride | 33.6 mg |
| mannitol | 55.5 mg |
| PEG4000 | 41 mg |
| PEG10000 | 20.2 mg |
| crospovidone | 12.5 mg |
| magnesium stearate | 1.5 mg |
| the separating layer | |
| hypromellose | 4.4 mg |
| talc | 5.0 mg |
| the enteric layer | |
| acrylic resin aqueous dispersion (L30D-55) | 35.5 mg |
| triethyl citrate | 1.2 mg |
| talc | 1.3 mg |

Manufacturing Process:

The operation of granulation and the separating layer referred to Example 2; the operation of the enteric layer was the same as Example 2 above.

Example 13

Enteric Tablet

Bill of Materials:

| the medicine core | |
|---|---|
| duloxetine hydrochloride | 33.6 mg |
| microcrystalline cellulose | 32.5 mg |
| PEG6000 | 25.1 mg |
| crospovidone | 8.1 mg |
| magnesium stearate | 1 mg |
| the separating layer | |
| hypromellose | 3.8 mg |
| talc | 5.7 mg |
| titanium dioxide | 0.8 mg |
| the enteric layer | |
| acrylic resin aqueous dispersion (L30D-55) | 30.7 mg |
| triethyl citrate | 1 mg |
| talc | 1 mg |

Manufacturing Process:

The operation of granulation, the separating layer and the enteric layer were the same as Example 2 above.

Example 14

Enteric Microtablet Capsule

Bill of Materials:

| the medicine core | |
|---|---|
| duloxetine hydrochloride | 33.6 mg |
| microcrystalline cellulose | 40.2 mg |
| PEG4000 | 20.1 mg |
| PEG8000 | 19.4 mg |
| xylitol | 13.7 mg |
| croscarmellose sodium | 2.9 mg |
| magnesium stearate | 0.5 mg |
| talc | 2.1 mg |
| the separating layer | |
| hypromellose | 4.2 mg |
| talc | 8.4 mg |
| titanium dioxide | 0.9 mg |
| the enteric layer | |
| acrylic resin aqueous dispersion (L30D-55) | 42.5 mg |
| triethyl citrate | 1.3 mg |
| talc | 1.3 mg |

Manufacturing Process:

The duloxetine hydrochloride, microcrystalline cellulose, PEG4000, PEG8000 and xylitol were mixed homogeneously and put into the high speed mixing granulator with the temperature of 80~85° C. in the jacket. The agitator of the granulator was turned on. When the temperature of the materials reached 60° C., stirring went on for another 6 minutes. The materials were gave out, cooled down, and granuled using 24 mesh sieve. The croscarmelose sodium and talc were added, mixed homogeneously and squashed to micro-tablets of 25 mg. Then the medicine core was obtained.

The operation of the separating layer referred to Example 3; the operation of the enteric layer was the same as Example 2 above.

The micro-tablets coated with the enteric layer were put into the capsule and the enteric micro-tablet capsule was obtained.

Example 15

Enteric Tablet

Bill of Materials:

| the medicine core | |
|---|---|
| duloxetine hydrochloride | 67.2 mg |
| microcrystalline cellulose | 20.5 mg |
| PEG4000 | 35.2 mg |
| PEG8000 | 33.4 mg |
| magnesium oxide | 15.0 mg |
| croscarmellose sodium | 3.4 mg |
| magnesium stearate | 2.0 mg |
| the separating layer | |
| hypromellose | 3.4 mg |
| talc | 7.3 mg |
| titanium dioxide | 0.7 mg |
| the enteric layer | |
| acrylic resin aqueous dispersion (L30D-55) | 35.0 mg |
| triethyl citrate | 1.1 mg |
| talc | 1.2 mg |

Manufacturing Process:

The operation of granulation and the separating layer referred to Example 1; the operation of the enteric layer was the same as Example 2 above.

Example 16

Enteric Granule (Extruding Granulation)

Bill of Materials:

| the medicine core | |
|---|---|
| duloxetine hydrochloride | 67.2 mg |
| microcrystalline cellulose | 20 mg |
| PEG6000 | 25 mg |
| poloxamer | 8 mg |
| crospovidone | 3 mg |
| sodium lauryl sulfate | 0.2 mg |
| talc | 3.7 mg |
| the separating layer | |
| hypromellose | 8 mg |
| talc | 4 mg |
| sucrose | 5 mg |
| the enteric layer | |
| HPMCAS-LF | 17 mg |
| triethyl citrate | 4.8 mg |
| talc | 5 mg |
| sodium lauryl sulfate | 0.5 mg |

Manufacturing Process:

The operation of granulation: the duloxetine hydrochloride, microcrystalline cellulose, PEG6000, poloxamer, crospovidone, sodium lauryl sulfate and talc were mixed homogeneously and put into the extruding machine with the warming temperature of 75~85° C. in the jacket. The wet materials were extruded through the sieve plate with the aperture of 1 mm by propeller propulsion to get the cylindrical banding extrudate which was cut off at once and made into granules after cooled down. And the fine powder was sieved out by 30 mesh sieve.

The operation of the separating layer: the solution of the separating layer was made according to Example 1. The separating layer was coated in the wurster fluidifying coating machine. The operation of the enteric layer: the solution of the enteric layer was made according to Example 3. The enteric layer was coated in the wurster fluidifying coating machine.

Example 17

Enteric Tablet

Bill of Materials:

| the medicine core | |
|---|---|
| duloxetine hydrochloride | 33.6 mg |
| PEG6000 | 11.76 mg |
| hydroxypropyl cellulose | 4.0 mg |
| croscarmelose sodium | 3.0 mg |
| carboxymethyl starch sodium | 3.0 mg |
| magnesium stearate | 0.56 mg |
| the separating layer | |
| hypromellose | 2.5 mg |
| talc | 1.4 mg |
| the enteric layer | |
| acrylic resin aqueous dispersion (L30D-55) | 17 mg |
| triethyl citrate | 0.6 mg |
| talc | 0.6 mg |

Manufacturing Process:

The operation of granulation, the separating layer and the enteric layer were the same as Example 2 above.

Example 18

Enteric Tablet

Bill of Materials:

| the medicine core | |
|---|---|
| duloxetine hydrochloride | 56 mg |
| PEG6000 | 22.4 mg |
| sucrose | 30 mg |
| crospovidone | 2.24 mg |
| magnesium stearate | 1.1 mg |
| the separating layer | |
| hypromellose | 4.18 mg |
| talc | 2.5 mg |
| mannitol | 3 mg |
| the enteric layer | |
| HPMCAS-LF | 9.5 mg |
| triethyl citrate | 2.6 mg |
| talc | 2.8 mg |
| sodium lauryl sulfate | 0.25 mg |

Manufacturing Process:

The operation of granulation and the operation of the separating layer were the same as Example 2 above.

The operation of the enteric layer was the same as Example 3 above.

Example 19

Enteric Tablet

Bill of Materials:

| the medicine core | |
|---|---|
| duloxetine hydrochloride | 33.6 mg |
| PEG6000 | 11 mg |
| sucrose | 14.0 mg |
| microcrystalline cellulose | 3.0 mg |
| sodium lauryl sulfate | 0.06 mg |
| the separating layer | |
| hypromellose | 2.5 mg |
| talc | 1.4 mg |
| the enteric layer | |
| acrylic resin aqueous dispersion (L30D-55) | 17 mg |
| triethyl citrate | 0.6 mg |
| talc | 0.6 mg |

Manufacturing Process:

The operation of granulation, the separating layer and the enteric layer were the same as Example 2 above.

Example 20

Enteric Tablet

Bill of Materials:

| the medicine core | |
|---|---|
| duloxetine hydrochloride | 44 mg |
| PEG6000 | 18 mg |
| sucrose | 4.0 mg |
| microcrystalline cellulose | 4.0 mg |
| polyoxyethylene castor oil | 1.0 mg |
| sodium stearyl fumarate | 0.6 mg |
| sodium lauryl sulfate | 1.1 mg |

| the separating layer | |
|---|---|
| hypromellose | 3.0 mg |
| sucrose | 2.0 mg |
| talc | 1.4 mg |

| the enteric layer | |
|---|---|
| acrylic resin aqueous dispersion (L30D-55) | 17 mg |
| triethyl citrate | 0.6 mg |
| talc | 0.6 mg |

Manufacturing Process:

The operation of granulation, the separating layer and the enteric layer were the same as Example 2 above.

The following trial examples are given as further illustrations of the beneficial effects of this invention.

Trial Example 1

As the hot-melt materials used in this invention were all water soluble, the dissolution and release of the main drug were accelerated and the biological availability of the medicine was enhanced. To verify the releasing rate of the duloxetine hydrochloride enteric tablet prepared by the hot melt granulation process used in this invention was better than that prepared by the common wet granulation process, the inventor prepared the duloxetine hydrochloride enteric tablet according to the two lists in the following table that were mainly the same in the prescription materials using the hot melt granulation process and the common wet granulation process, respectively, and the releasing rate of the two samples were compared.

Bill of materials of the prescription compared the medicine cores:

| the material list of the hot melt granulation process | | the material list of the common wet granulation process | |
|---|---|---|---|
| duloxetine hydrochloride | 10 mg | duloxetine hydrochloride | 10 mg |
| Povidone K30 | 3.64 mg | Povidone K30 | 3.64 mg |
| sucrose | 125 mg | sucrose | 125 mg |
| lactose | 75 mg | lactose | 75 mg |
| PEG6000 | 34 mg | 60% (wt) ethanol | 20 mg |
| magnesium stearate | 1.33 mg | magnesium stearate | 1.33 mg |

Bill of materials of the separating layer and the enteric layer:

| the separating layer | |
|---|---|
| hypromellose | 10 mg |
| talc | 6 mg |
| sucrose | 4 mg |

| the enteric layer | |
|---|---|
| acrylic resin aqueous dispersion (L30D-55) | 45 mg |
| triethyl citrate | 1.5 mg |
| talc | 1.5 mg |

The process of the medicine core of the hot melt granulation: The duloxetine hydrochloride, sucrose, lactose, povidone K30 and PEG6000 were mixed homogeneously, and placed into the high speed mixing granulator with the temperature in the jacket of 80~85° C. The agitator of the granulator was turned on. When the temperature of the materials reached 60° C., the agitation went on for 6 min. The materials were gave out, cooled down, and granuled using 24 mesh sieve. The magnesium stearate was added, and mixed homogeneously, and squashed. Then the medicine core was obtained.

The process of the medicine core of the common wet granulation: the povidone K30 was dissolved in the solution of 60% (wt) ethanol. The duloxetine hydrochloride was added, and after it was dissolved, the sucrose and the lactose were added and stirred to soft materials in the groove shaped mixer. The wet granules were made using the oscillating granulator (fitted with 20 mesh nylon net). The wet granules were dried at 50~60° C. in the convection oven, then cooled down, and granulated using the 20 mesh sieve. The magnesium stearate was added, mixed homogeneously, and squashed. Then the medicine core was obtained.

The operation of the separating layer and the enteric layer coated out the medicine core mentioned above were the same as Example 2 above, respectively. The two portions of duloxetine hydrochloride enteric tablet were respectively put into a high density polyethylene plastic bottle. Then the bottle was sealed up and put into an accelerated testing box. And the contrasted stability (the data of releasing rate) was studied at the temperature of 40° C.±2° C. and the relative humidity of 75%±5%.

According to the assay method of the enteric formulation described in the appendix of Pharmacopoeia of the People's Republic of China (2005) Volume II, 900 ml of the phosphate buffer (pH6.8) was used as the release medium, the rotational speed was 100 r/min, and the releasing rate of the two samples was determined. The results are as follows:

| Samples | The releasing rate of the duloxetine hydrochloride enteric tablet prepared by the hot melt granulation process | The releasing rate of the duloxetine hydrochloride enteric tablet prepared by the common wet granulation process |
|---|---|---|
| accelerated testing 0 month | 95% | 85% |
| accelerated testing 3 months | 94% | 80% |
| accelerated testing 6 months | 95% | 81% |

Trial Example 2

As in this invention the medicine core of the enteric formulation of duloxetine or its salt was prepared using the hot-melt process, it avoided the introduction of water or organic solvents, reduced the residual of solvents, also decreased the degradation of duloxetine, and increased the stability of the formulation in preparation and storage. The inventor compared the stability of the enteric tablet prepared in Example 5 and that prepared in Trial Example 1 using the common wet granulation process. The two portions of duloxetine hydrochloride enteric tablet were put into a high density polyethylene plastic bottle. Then the bottle was sealed up and put into an accelerated testing box. And the stability (the total amount of the impurity) was contrasted and inspected after they were placed at the temperature of 40° C.±2° C. and the relative humidity of 75%±5% for 6 months.

Figure 2:
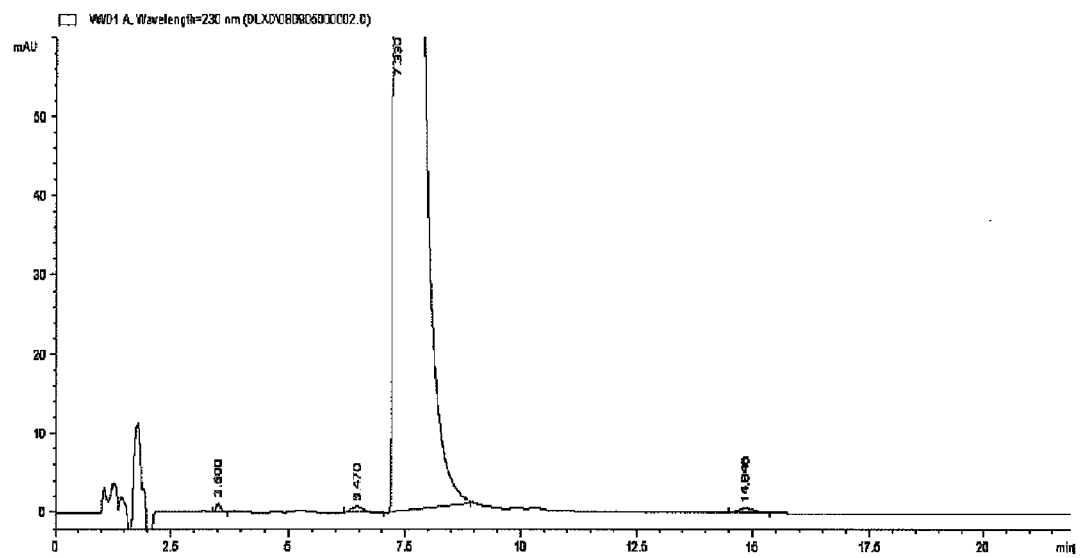
FIG. 2 is the determination spectrogram of related substances of the medicine core of duloxetine hydrochloride prepared in Example 5, which is sealed up in high density polyethylene bottle and placed in the temperature of 40° C.±2° C. and the relative humidity of 75%+5%.

Testing Method: the phosphate buffer (pH5.8)-acetonitrile (63:37) was used as the mobile phase, and the determine wavelength was 230 nm. The solution of the two samples was taken accurately and injected into HPLC. The chromatogram was recorded to the time that was two times of the retention time of the main peak. The data of the total amount of the impurity was as follows. The HPLC chromatogram were to see FIG. 1 and FIG. 2, respectively.

| Samples | The content of the impurity of the duloxetine hydrochloride enteric tablet prepared in Example 5 of this invention | The content of the impurity of the duloxetine hydrochloride enteric tablet prepared by the common wet granulation |
|---|---|---|
| accelerated testing 0 month | 0.08% | 0.08% |
| accelerated testing 3 months | 0.14% | 0.33% |
| accelerated testing 6 months | 0.25% | 0.57% |

Trial Example 3

The inventors have the opinion that sugar and sugar alcohol, especially sucrose, mannitol, xylitol and maltitol, were beneficial to the release of the main drug from the medicine core. However, using lactose as the main filler would affect the stability of the formulation. So lactose was not the preferable filler.

Made one portion of medicine core as Example 5 and made another portion of medicine core in the same manner as Example 5 but using lactose instead of sucrose. The two portions of medicine core were coated with the separating layer and the enteric layer in the same manner as Example 5 above respectively.

The two portions of duloxetine hydrochloride enteric tablet were put into a high density polyethylene plastic bottle respectively. Then the bottle was sealed up and put into an accelerated testing box. The stability, namely the releasing rate and the total amount of the impurity, was contrasted and inspected after they were placed at the temperature of 40° C.±2° C. and the relative humidity of 75%±5% for 6 months.
Contrasted Prescribe:

| list of materials of the medicine core in Example 5 of this invention | | list of materials of the contrasted sample | |
|---|---|---|---|
| duloxetine hydrochloride | 30 mg | duloxetine hydrochloride | 30 mg |
| sucrose | 100.6 mg | lactose | 100.6 mg |
| PEG6000 | 33.4 mg | PEG6000 | 33.4 mg |
| microcrystalline cellulose | 28.0 mg | microcrystalline cellulose | 28.0 mg |
| crospovidone | 2.1 mg | crospovidone | 2.1 mg |
| magnesium stearate | 1 mg | magnesium stearate | 1 mg |

The releasing rate was determined according to the method as that in Trial Example 2. The data were follows:

| Samples | The releasing rate of the duloxetine hydrochloride enteric tablet prepared in Example 5 | The releasing rate of the contrasted sample |
|---|---|---|
| accelerated testing 0 month | 95% | 85% |
| accelerated testing 3 months | 96% | 80% |
| accelerated testing 6 months | 93% | 78% |

The total amount of the impurity was determined according to the method as that in Trial Example 2. The data were follows:

| Samples | The total amount of the impurity of the duloxetine hydrochloride enteric tablet prepared in Example 5 | The total amount of the impurity of the contrasted sample |
|---|---|---|
| accelerated testing 0 month | 0.08% | 0.11% |
| accelerated testing 3 months | 0.14% | 0.45% |
| accelerated testing 6 months | 0.30% | 1.21% |

What is claimed is:

1. A medicine core of duloxetine enteric formulation, consisting of pharmaceutical active ingredient duloxetine or its salt and pharmaceutically acceptable excipient; wherein the pharmaceutically acceptable excipient contains water-soluble hot melt materials, the content of which is 10% to 40% by mass relative to the total mass of the medicine core; the content of pharmaceutical active ingredient duloxetine or its salt is 15% to 60% by mass relative to the total mass of the medicine core; and the rest is at least one other pharmaceutically acceptable excipient; wherein the softening or melting temperature of the said water-soluble hot melt material is 40 to 65° C.,
   wherein the medicine core of the duloxetine enteric formulation is prepared by a manufacturing process comprising:
   mixing duloxetine or its salt, water-soluble hot melt material and pharmaceutically acceptable excipient,
   heating the water-soluble hot melt materials until they are softened or melted; and
   granulating in the state that the water-soluble hot melt materials are softened or melted, and then cooling down.

2. The medicine core according to claim 1, wherein the duloxetine salt is duloxetine hydrochloride.

3. The medicine core according to claim 1, wherein the at least one other pharmaceutically acceptable excipient is one or more excipients selected from the group consisting of a filler, disintegrant, lubricant and surfactant.

4. The medicine core according to claim 3, wherein the filler is one or more fillers selected from the group consisting of sucrose, mannitol, xylitol, maltitol, hydroxypropyl-β-cyclodextrin, microcrystalline cellulose, pregelatinized starch, magnesium oxide, arginine, sodium carbonate, sodium bicarbonate and magnesium carbonate; and the content of the filler is 10% to 65% by mass relative to the total mass of the medicine core.

5. The medicine core according to claim 3, wherein the disintegrant is selected from the group consisting of sodium starch glycolate, hydroxypropyl cellulose, crospovidone and croscarmellose sodium; and the content of the disintegrant is 1% to 18% by mass relative to the total mass of the medicine core.

6. The medicine core according to claim 3, wherein the lubricant is one or more lubricants selected from the group consisting of magnesium stearate, colloidal silicon dioxide, sodium stearyl fumarate and talc; and the content of the lubricant is 0.1% to 3% by mass relative to the total mass of the medicine core.

7. The medicine core according to claim 3, wherein the surface active agent is selected from the group consisting of polysorbate 80, polyoxyethylene castor oil and sodium lauryl sulfate; and the content of the surface active agent is 0.1% to 1.5% by mass relative to the total mass of the medicine core.

8. A method of manufacturing the medicine core of the duloxetine enteric formulation according to claim 1, comprising:
   mixing duloxetine or its salt, water-soluble hot melt material and pharmaceutically acceptable excipient,
   heating the water-soluble hot melt materials until they are softened or melted; and granulating in the state that the water-soluble hot melt materials are softened or melted, and
   then cooling down.

9. The manufacturing process according to claim 8, wherein the granulation is a hot melting stirring granulation, hot melting fluidifying granulation or hot melting squeezing granulation.

10. A duloxetine enteric formulation, which contains a medicine core, a separating layer and an enteric layer, wherein the medicine core is the medicine core of claim 1.

11. The duloxetine enteric formulation according to claim 10, wherein the duloxetine enteric formulation is an enteric coated tablet, an enteric granules or an enteric micro-tablet capsule.

12. The duloxetine enteric formulation according to claim 10, further comprising a modified layer outside the said enteric layer.

13. A method of making a duloxetine enteric formulation, which contains a medicine core, a separating layer and an enteric layer, wherein the medicine core is the medicine core according to claim 1, and wherein the process comprises
   step (1) coating the medicine core of claim 1 with a separating layer to obtain an object; and
   step (2) coating the object obtained by step (1) with an enteric layer to obtain another object.

14. The method of making the duloxetine enteric formulation according to claim 13, further comprising step (3) coating the object obtained by step (2) with a modified layer.

15. The medicine core according to claim 1, wherein the water-soluble hot melt materials include one or more ingredients selected from the group consisting of polyethylene glycol, poloxamer and polyoxyl (40) stearate.

16. The medicine core according to claim 15, wherein the polyethylene glycol is one or more selected from polyethylene glycol 4000 to 10000.

* * * * *